United States Patent [19]

Haak et al.

[11] Patent Number: 5,573,529

[45] Date of Patent: Nov. 12, 1996

[54] COLOR CODED MEDICAL INSTRUMENTS

[76] Inventors: Benjamin A. Haak, 506 N. Home; James T. Diffendal, 1112 S. Lincoln, both of Park Ridge, Ill. 60068

[21] Appl. No.: 332,115

[22] Filed: Oct. 31, 1994

[51] Int. Cl.$^6$ .............................................. A61B 17/00
[52] U.S. Cl. .............................................. 606/1; 128/898
[58] Field of Search ...................... 606/41–52, 1, 606/205–209; 128/898

[56] References Cited

U.S. PATENT DOCUMENTS

| | | |
|---|---|---|
| 3,627,859 | 12/1971 | Mesiti et al. . |
| 3,740,779 | 6/1973 | Rubricuis . |
| 3,747,603 | 7/1973 | Adler . |
| 3,840,015 | 10/1974 | Gain . |
| 3,930,886 | 1/1976 | Mesiti et al. . |
| 3,935,640 | 2/1976 | Cohan . |
| 4,117,791 | 10/1978 | Current et al. ............ 112/222 |
| 4,140,125 | 2/1979 | Smith . |
| 4,202,351 | 5/1980 | Biche . |
| 4,229,420 | 10/1980 | Smith et al. . |
| 4,253,830 | 3/1981 | Kazen et al. . |
| 4,671,916 | 6/1987 | Hamas . |
| 4,882,867 | 11/1989 | Lindén . |
| 4,897,037 | 1/1990 | Appleby . |
| 4,982,627 | 1/1991 | Johnson . |
| 5,062,173 | 11/1991 | Collins et al. ............... 7/118 |
| 5,275,612 | 1/1994 | Bales, Jr. . |
| 5,280,967 | 1/1994 | Varrin, Jr. .................. 285/93 |

OTHER PUBLICATIONS

Brady, George S. and Clausen, Henry R., *Materials Handbook*, 11th Edition, "Fluoroplastics", (1977), p. 374.
Brady, George S. and Clauser, Henry R., *Materials Handbook*, 13th Edition, "Fluoroplastics", (1991), p. 345.
Dagani, Ron, *C&EN*, "New, Simpler Process Forms Copper Circuits Directly on Teflon", (Jan. 1992), pp. 24–25.
Ash, Michael & Irene, *Handbook of Plastic Compounds Elastomer, Resin PV International Guide*, "Fluoropolymers", (1992), pp. 134–136.
Michael Berins, ed., *SPI Plastics Engineering Handbook of the Society of the Plastics Industry, Inc.*, 5th ed., "TFE–fluoroplastic", (1991), p. 715.
*Encyclopedia of Polymer Science and Engineering*, vol. 16, "Tetrafluoroethylene Polymers", (1989) pp. 577, 592–593.
*Dictionary of Chemistry*, "Urethane Resins (Polyurethanes)", (1985), p. 293.
Rez–Tech, Inc., Salisbury, NC, Product Information Sheet, "*Coating Technology from Rez–Tech, Inc.*", 1993.
National Design Engineering Show & Conference, Mar. 8–11, 1993, p. 145 of Show Program, Chicago, IL.

*Primary Examiner*—Angela D. Sykes
*Assistant Examiner*—Michael Peffley
*Attorney, Agent, or Firm*—Grady J. Frenchick; Strout, Stroud, Willink, Thompson & Howard; Theresa J. Welch

[57] ABSTRACT

The method of identifying sets of metal medical instruments includes the steps of creating a color plan for identifying metal medical instruments, providing at least one medical instrument having a metal portion electro-depositing at least one colored water-borne polyurethane coating on the metal portion of each metal medical instrument in accordance with the plan. Each of the coatings is deposited in a layer which is thick enough to adhere to the instrument but not so thick as to crack or flake off the instrument. Each of the coatings is resistant to sterilization conditions with each color of the coatings contrasting with the instrument and with any other electro-deposited coating. The method further provides for allowing the coating to cure a temperature in the range of 270° F.–350° F. for a time period in the range of 2 minutes to 50 minutes. The method is preferably used to electro-deposit the coating on stainless steel, aluminum, chrome or silver plated instruments with the method most preferably being used on surgical grade stainless steel instruments. Kits and medical instruments are disclosed.

44 Claims, 8 Drawing Sheets

COLOR CODED MEDICAL INSTRUMENTS

FIELD OF THE INVENTION

This invention relates generally to the field of medical instrument management. In particular, this invention relates to identifying hand held medical tools or instruments as belonging to a set or group. The invention is particularly well suited for identifying sets of stainless steel medical or surgical instruments by color coded indicia.

BACKGROUND OF THE INVENTION

In today's cost-conscious health care environment, health care providers are constantly looking for ways to improve the delivery of quality care to their patients. In instances where the patient requires a specific medical procedure utilizing hand held medical or surgical instruments, these instruments are gathered and sterilized as sets, e.g., tray set-ups, for the patient's specific medical procedure. Thus, for example, a cardiac procedure will have a set, collection or "tray" of instruments, an ophthalmology procedure a different set of instruments, and so forth. Also, for example, different medical specialty departments in the hospital use different instruments. Medical instrumentation or collections of instruments, e.g. trays, today are so specific that often only the particular department which purchased the instrument knows where it goes and what it does. In addition, certain types of medical instrument sets for medical procedures may be organized according to the manufacturer of the instruments or according to the user of the instrument.

The preparation of the tray set ups or operating room trays for invasive medical procedures is a critical function of the medical instrument manager typically, the operating room manager or nurse supervisor. The medical instrument manager must ensure the integrity, sterility, and functionality of the individual instruments as well as the correct organization of sets of instruments into trays for medical procedures. A further responsibility of this person is the inventory and tracking of instruments. Thus it is necessary to be able to identify an inventory of the medical instruments to facilitate, repair and replace the instruments should they become broken or worn.

During a medical or surgical procedure, it is important for the medical personnel to have the correct instruments present, especially correct specialty instruments, placed in the correct trays and also to be able to readily and easily identify and confirm that the proper instruments are indeed present for the medical procedure. For instrument management, it is also important to minimize the number of steps involved in identification and maintenance of the instruments.

In any medical procedure, the instruments require cleaning and sterilization between uses. As is known in the medical arts, the sterilization process typically includes the use of a steam autoclave, rapid sterilization methods, or exposure to chemically active substances. Autoclave manufacturers prepare specific directions for the operation of the autoclave in respect to temperature, time and pressure settings. Typically the autoclave treatment is as follows: Steam treatment under pressure of approximately 30 pounds per square inch(psi) at a temperature of 270° F.(Fahrenheit) for a time period of 50–80 minutes. This time period typically includes a 20–30 minute drying time. A rapid sterilization method requires that the instruments be "flashable". By flashable is meant rapid autoclave sterilization of an instrument using steam treatment under pressure of approximately 30 psi at a temperature of 270° F. for a time period of 3 to 10 minutes depending on the instrument's weight and number of instruments being autoclaved. Alternatively chemical sterilization agents such as CIDEX® (Johnson & Johnson Company of Racine, Wis.) are used to chemically sterilize medical instruments.

The sterilized sets are delivered to the appropriate operating room, examining room or department where the medical procedure will occur. The rapid sterilization technique is also sometimes used in the operating room when an instrument necessary for a medical procedure falls off of a sterile surface. It is quickly cleaned and rapidly sterilized using the "flashable" sterilization technique previously described, thereby allowing for minimal time interruption in the medical procedure.

After the procedure is completed the instruments are identified, inventoried, cleaned, and examined for needed repair before being sorted into sets and sterilized for subsequent reuse on another patient. The instruments may be jostled against each other after use and prior to the sterilization process, as well as when the instruments are sent out for repair or replacement. Thus it is necessary to be able to identify an inventory of the medical instruments to facilitate, repair and replace the instruments should they become broken or worn.

In the past, color coding schemes for organizing medical or surgical instruments have included applying indicia such as color coding vinyl tapes, dipping the instruments in nylon, TEFLON® (E. I. DuPont de Nemours & Co., Willmington, Del.) or other plastic dipping solutions, and applying powder coating and colored bonding tapes to the handling surfaces and adjacent areas of the instruments. Each of these methods has drawbacks.

Color coding tapes can be bothersome to surgeons because the tapes roll and stick to surgical gloves. A number of layers of the tape are frequently wound over each other on the medical instrument surfaces sought to be color coded. Further, after repeated washing, decontamination and sterilization, and with normal jostling of instruments, the tape will loosen, tear and fall off. Thus, the instruments require continual retaping, which must be preceded by the labor intensive process of removal of the residual layers of tape and subsequent manual cleaning of the glue residues. The glue on the tape is also of concern because it may harbor harmful bacteria.

Plastic dipping materials such as the nylon TEFLON® have the advantage of being quite visible; however, the material is too heavy and thick to apply to micro forceps and spring handled instruments and it is nearly impossible to apply to double ended instruments. Also, the plastic dipping materials crack and chip over time and are not "flashable" as described above, because of the nylon or plastic material's heat insulating properties.

In the bonding tape process, tiny color chips are adhered to the instruments with a colorless bonding material. This method suffers from two disadvantages, the chips are very hard to see because they are so small and the chips can peel off if the bonding material is damaged. In addition, the bonding tape is difficult to apply to knurled or ridged surfaces. Plastic dipping materials and colored bonding tapes suffer the additional drawback of being relatively easily removable, especially in the harsh environment to which they are exposed.

In addition to these methods, color coded stainless steel surgical instruments have been introduced onto the market that have paint applied to the handles. The paint application process is not effective because the paint does not bond to the stainless steel surfaces. The paint tends to flake after repeated autoclaving and generally has a very short life span. Also, the painted sets chip upon handling and jostling against other instruments.

Some prior art patents purport to deal with some of the problems created by the use of sticky tape and cracking and peeling coatings on surgical instruments. In U.S. Pat. No. 4,671,916, color coded medical instruments are disclosed which use a colored plug which may have a distinctively shaped bore head. The plug is preferably made of autoclavable material which is inserted in a bore formed in the instrument. The bore into which the plug is secured is 1/32 to 1/4 inch in diameter. The plug may be used to retrofit older instrument sets. However, the color coded plug area is small and requires close scrutiny to identify the instrument as belonging to a particular set.

In U.S. Pat. No. 4,882,867, color coding of a dental instrument is taught where the color coded part is a three dimensional sleeve, ring or disc mounted on a shaft before the formation of a handle by an injection moulding method. This method is not adaptable to retrofit older instrument sets.

U.S. Pat. No. 3,747,603 discloses a surgical kit including a set of cervical dialators having probes of different diameters and handles of identical size and configuration. The handles can be color coded to indicate the probe diameter.

U.S. Pat. No. 3,935,640 discloses a double ended dental instrument with a color coded probe on one end of the instrument. In use, the color coding shows the depth to which the instrument probe has penetrated the periodontal tissue of the mouth.

U.S. Pat. No. 3,840,015 discloses a non-toxic photoluminescent material that is either coated upon a portion of a metallic surgical device, such as an instrument's blade or needle tip, or impregnated within a porous surgical device such as a suturing thread or sponge. With the use of an appropriate exciting light source to illuminate the photoluminescent material, the exact position, relationship and movement of the devices are observed during the medical procedure.

U.S. Pat. No. 3,740,779 shows a surgical scalpel which includes a thermoplastic shaft which is color coded to allow identification of the size and shape of the cutting blade of the instrument.

U.S. Pat. No. 4,253,830 discloses a portable bur block for holding dental burs, using removable elastomeric insert receptacles that may be color coded and arrangeable and rearrangeable in the bur block in an organized manner for ready identification and accessibility of the dental burs.

U.S. Pat. No. 5,275,612 shows the use of color coding a ferrule to signify the type of surgical instrument of which it is a part.

U.S. Pat. No. 4,202,351 discloses an identification means for the ends of lead wires of electrocardiographic monitoring instruments consisting of color coded identification rings having raised indicia which is also color coded to the conventions used in the electrocardiography art to correspond to anatomical locations. The identification ring and raised letters are fabricated or molded of a thermoplastic material with the raised letters forming an integral part of the identification ring but with the raised letters being of a different colored material than the remainder of the ring.

Despite recognition and study of the various aspects of instrument management for hand held medical or surgical instrument identification, the prior art has produced very little in the way of inexpensive, practical techniques for producing a method of identification of sets of instruments by color coding old and new medical or surgical instruments with a permanent color material which is visible under ambient surgical or medical examining room lighting conditions. Nor is there an instrument management system utilizing a color coded system which won't crack or chip off during use, won't impede use by shrinking ring size, and won't leave a sticky tape residue. Additionally, there appears to be problems providing a color coding system which can be applied to knurled, micro and spring type instruments without impeding functionality and which allows for center application for double ended instruments. It is further appreciated that an instrument management system is needed which utilizes a color coding system which can be used on stainless steel, chrome, aluminum or silver plated instruments in a very thin color coded material layer.

SUMMARY OF THE INVENTION

The present invention provides a method of identifying sets of metal medical or surgical instruments comprising the steps of: a) creating a color plan for identifying metal medical instruments; b) providing at least one medical instrument having a metal portion; c) electro-depositing at least one colored water-borne polyurethane coating on the metal portion in accordance with the plan, each coating being resistant to sterilization conditions, each color of coating contrasting with instrument and, where more than one colored coating has been electro-deposited contrasting with any other colored coating; and d) allowing each coating to cure at a temperature in the range of 270° F. to 350° F. for a time period in the range of 2 minutes to 50 minutes. Most preferably the curing step occurs at 320° F. for a time of 20 minutes. By medical instrument is meant hand held medical or surgical instruments used in medical or surgical procedures on patients. The method may be used on new or existing stainless steel, aluminum, chrome or silver plated instruments. Most preferably the coating is electro-deposited on stainless steel medical instruments.

The method of the present invention is applicable to medical instruments having smooth surfaces as well as those with complex surface characteristics including textures, convolutions, ridges, concave/convex regions and the like. Knurled, spring handled, double ended instruments and micro surgical instruments also may be marked in accordance with the present invention without impeding functionality. The coating is electro-deposited onto the metal portion of the medical instrument which is handled, i.e., grasped or held by the user, i.e., metal handles of medical instruments. Coating may also be applied to adjacent parts, such as the shank parts adjacent to the finger rings on scissors or clamping instruments. Coatings may be applied to handling surfaces of double ended instruments, spring handled instruments and micro instruments. A plurality of differently colored water-borne polyurethane coating may be electro-deposited on the handle portion of the instrument. Where the instrument has a shank portion, a plurality of colored water-borne polyurethane coatings may be electro-deposited on a shank portion of the instrument. Where the instrument is double ended with the metal portion disposed between the ends, the coating material may be electro-deposited on all or part of the metal portion.

The method further comprises the step of sorting the instruments into a set to be utilized for specific medical procedures by grouping the instruments with other instruments similarly color coded, wherein the instruments are selected for the sorting by the instruments possessing a common colored coating.

The method further comprises electro-depositing the coating to substantially cover the handling surface and/or adjacent areas, thereby allowing a user to easily identify instrument without close scrutiny of the instrument. The method also further comprises the use of color coding which is readily visible under normal hospital and clinic lighting conditions and which does not require special lighting to view the colored coating. In addition, the coating maintains its integrity against chipping, cracking, breaking, peeling and sticking after 500 autoclave cycles where the coating is maintained a 270° F. at approximately 30 pounds per square inch (psi) pressure in steam for approximately 35 minutes of time. The coating is also flashable at an autoclave sterilization cycle of the instrument using steam treatment under pressure of approximately 30 pounds per square inch at a temperature of 270° F. for a time period of 3 to 10 minutes depending on the weight of the instrument.

Preferably the coating is electro-deposited according to the present invention onto a medical instrument having a non-invasive portion and an invasive portion with the coating electro-deposited upon the non-invasive portion.

The present invention also comprehends a medical instrument having colored indicia on a surface thereof, the indicia comprising electro-deposited colored water-borne polyurethane coating, the indicia being peel resistant, capable of being multiply autoclaved and conformable to a contour of the surface. Preferably, the metal surface is stainless steel, aluminum, chrome or silver plated and the indicia is electro-deposited thereon. The indicia is electro-deposited onto a handle portion of the instrument. The invention further comprehends that a second indicia comprising a differently colored water-borne polyurethane coating is electro-deposited adjacent to the first indicia on the metal surface of the instrument. The invention still further comprehends that a plurality of indicia comprising differently colored water-borne polyurethane coatings are electro-deposited onto separate areas of a metal surface of the instrument.

The medical instrument may be double ended with the metal surface disposed between the ends and with the indicia electro-deposited on all or a portion of the metal surface disposed between the ends. Alternatively, the medical instrument is a spring handled type instrument, or the medical instrument is a micro surgical instrument, or the medical instrument has a knurled handled metal surface.

Preferably, the indicia is electro-deposited onto a stainless steel medical instrument.

The invention further comprehends a kit or tray of medical instruments comprising a collection of medical instruments selected for a specified medical procedure, each of the medical instruments having one commonly colored indicia on a metal surface thereof, the indicia comprising electro-deposited colored water-borne polyurethane coating, the indicia being peel resistant, capable of being autoclaved and conformable to a contour of the surface, the color being used to identify the specific medical procedure, each coating deposited in a micro thin layer thickness, the color of the coating contrasting with the instrument and where more than one colored coating has been electro-deposited, each colored coating also contrasting with any other colored coating. The coating micro thin layer thickness comprises a layer thick enough to adhere to the medical instrument but not so thick as to crack or flake off the medical instrument. Preferably the micro thin layer thickness ranges from 0.1 mils to 0.5 mils.

The kit or tray of the present invention also includes instruments having at least one additional differently colored indicia, with the additional differently colored indicia indicating the instrument may also be used in another kit or tray for a different medical procedure. The kit or tray of the present invention also includes instruments having at least one additional differently colored indicia, with the additional differently colored indicia indicating that the instrument belongs to a particular medical specialty group. The kit or tray of the present invention also includes instruments having at least one additional differently colored indicia, with the additional differently colored indicia indicating that the instrument is used by a particular user. The kit or tray of the present invention also includes instruments having at least one additional differently colored indicia, with the additional differently colored indicia indicating that the instrument is produced by a particular manufacturer.

An advantage of the present invention is that a reduction in time involved in matching up single misplaced instruments and putting them back in the primary case tray is expected. This is expected to result in large labor saving costs and in the elimination of frustration of nursing, clinic and hospital staff in preparing the case trays.

Use of the method of identifying sets of medical instruments of the present invention enables the medical instruments manager to more quickly and easily visually identify, inventory and assemble instruments. The present invention helps in the management of instruments and minimizes theft in that the instruments are specifically color coded according to the color plan so stolen items are permanently identified and, therefore, less marketable. Further, use of such color coded instruments eliminates the need for periodically replacing a nonpermanent coding system and constant checking of the instruments to assess whether repair or replacement of the nonpermanent coding system is necessary. In addition, the present invention is extremely advantageous to medical personnel since they no longer will need to be concerned with the problem of potentially cracking, peeling or sticky color coding materials on the instruments which can slow procedures and puncture or tear gloves.

The identification system may be advantageously retrofitted to existing stainless steel, aluminum, chrome and silver plated instruments and is especially preferable for use on surgical grade stainless steel instruments. In many cases, the prior art color coding materials are not workable with respect to stainless steel instruments and can not be retrofitted to existing instrument sets.

An advantage of the medical or surgical instrument marked in accordance with the method of this invention is that the instruments will withstand repeated handling and autoclave sterilization without the color coded coating chipping, peeling or cracking. If under severe conditions a chip or crack occurs, the integrity of the coating is not jeopardized.

Another advantage of the present invention is that the color coded surfaces allow for ease of cleaning. The coating does not become sticky with repeated usage.

An additional advantage of the present invention is that the coating can cover the entire handling surface and adjacent areas thereby allowing the user to easily identify the instrument without close scrutiny.

Utilization of highly visible coating materials of the present invention which do not require special excitation lighting is advantageous because it is not necessary to expend extra resources for special lighting. Existing fluorescent and incandescent lighting systems are used to view and identify the color coded coating portions of the instruments.

All of the advantages result in substantial time and cost savings.

Other advantages and a fuller appreciation of the specific attributes of this invention will be gained upon examination of the following drawings, detailed description of the preferred embodiments, and the appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which.

DETAILED DESCRIPTION OF THE PREFERRED EMBODIMENT

Figure 9:
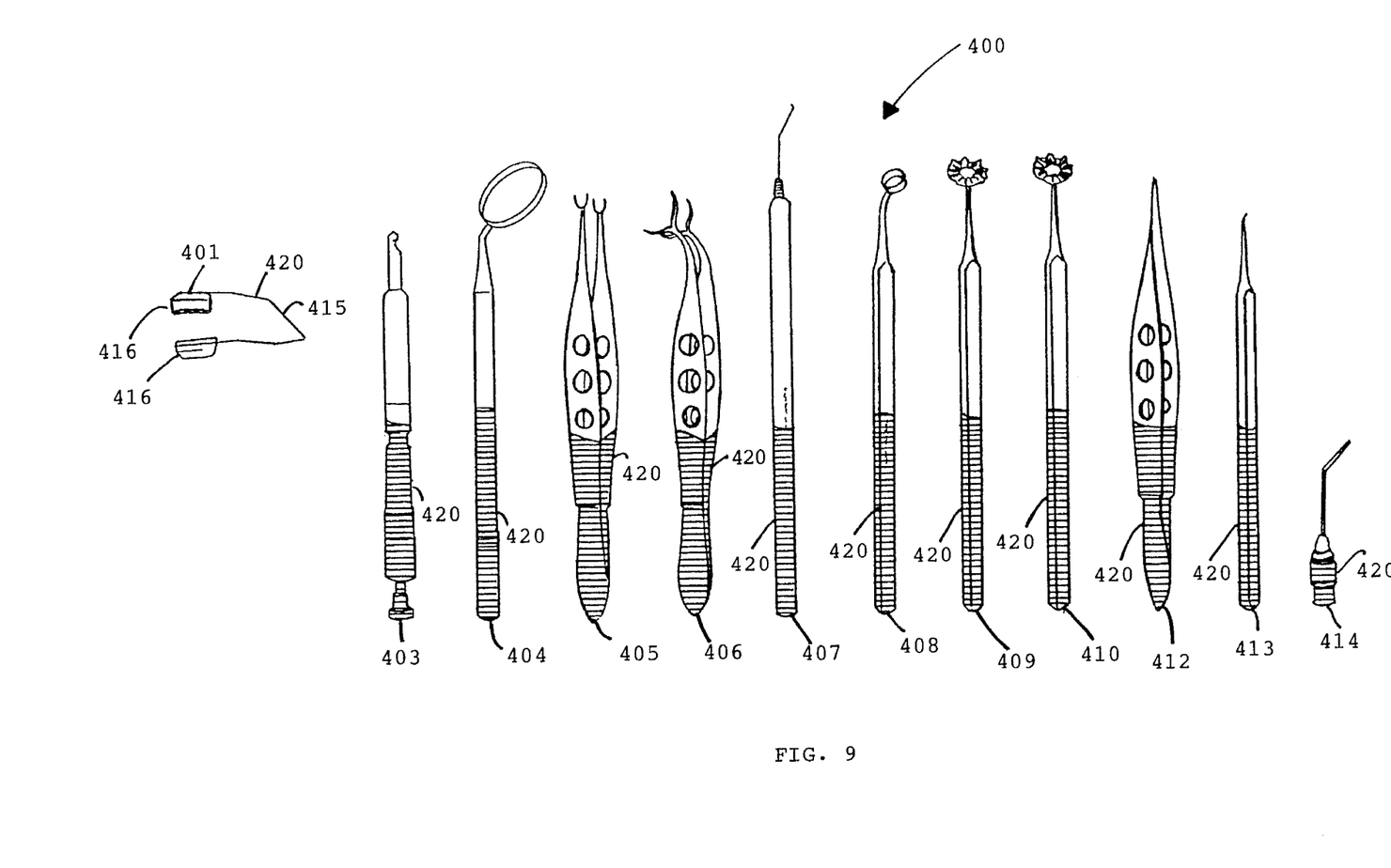
FIG. 9 is a view of a kit of medical instruments having a color coding identification system of the present invention.
Figure 10:
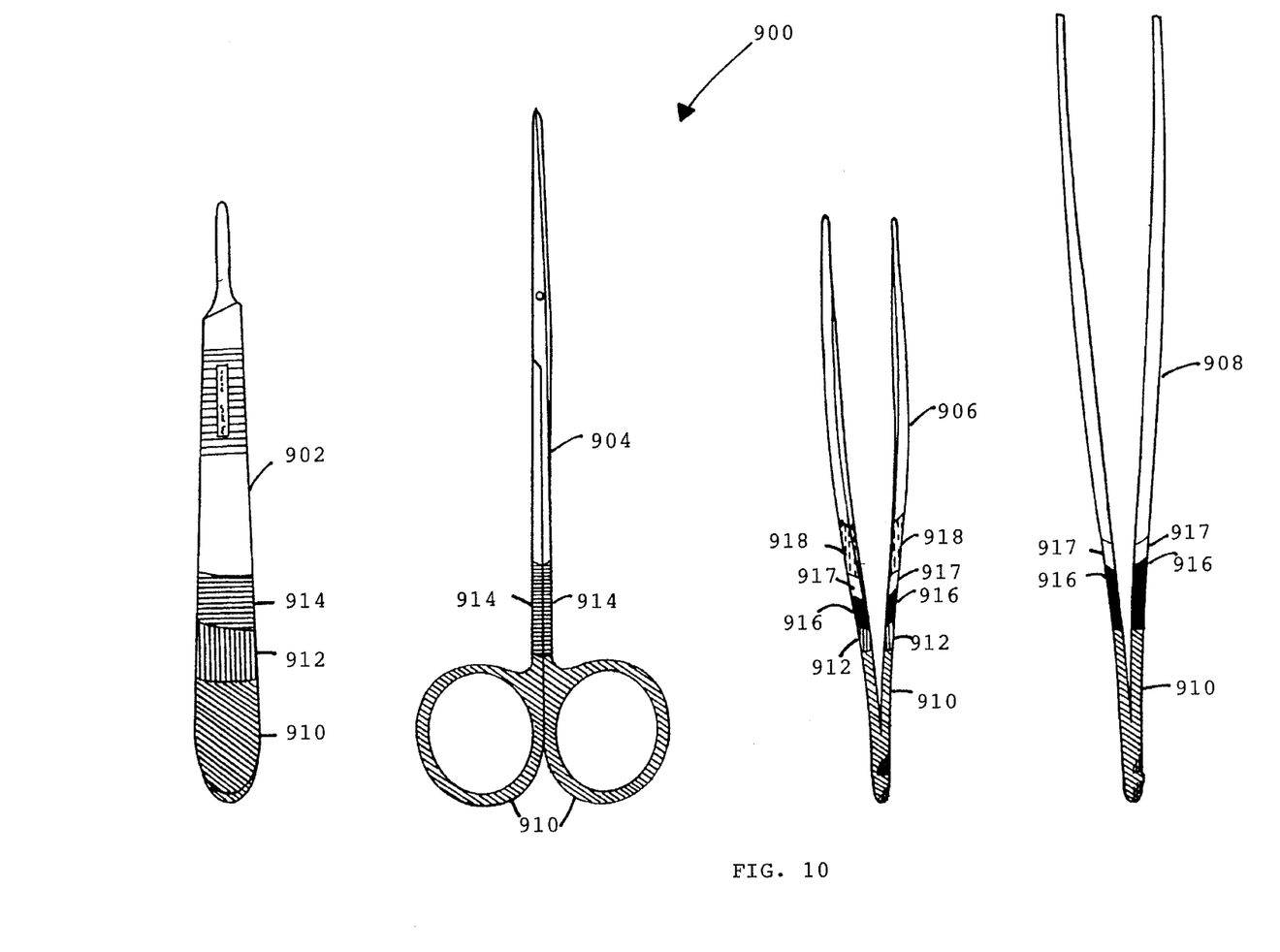
FIG. 10 is a top view of another kit of medical instruments having multiple color indicia electro-deposited according to the present invention.

Referring now to FIGS. 1(a) through 1(c), 2(a)–2(f), 3(a)–3(c), 4, 5(a)–5(c), 6(a)–6(b), 7 and 8 show exemplary medical instruments that utilize the method of identifying sets of metal medical instruments utilizing at least one colored water-borne polyurethane coating electro-deposited on a metal surface of each medical instrument. FIGS. 9 and 10 show exemplary kits of medical instruments with each instrument prepared according to the method of the present invention.

To practice the method of the present invention, first a color plan is created for identifying metal medical instruments. By medical instrument is meant hand held medical or surgical instruments used in medical or surgical procedures on patients. The plan assigns specific colors to specific medical procedures, and/or specific medical specialty groups, and/or specific users, and/or specific manufactures. Other categories for color assignment may be made as the user so wishes. Thus, one or more colored indicia may be applied to the instrument. The color plan includes, but is not limited to, choice of color indicia and selection of the location of color indica on the instrument. Recognition of particular colors and association of those colors with specific medical procedures allows the users and maintainers of the instruments to quickly identify and to sort the instruments into respective sets for use in specific medical procedures.

Secondly, the method requires at least one medical instrument having a metal portion. The method of this invention is used on metal medical instruments. A portion of the medical instrument is identified for the electro-deposition of the colored water-borne polyurethane coating in accordance with the color plan. Metal medical instruments typically have an invasive portion and a noninvasive portion. By invasive portion is meant that part or portion of the medical or surgical instrument that punctures, cuts or penetrates into the tissue, bone or other body parts of a patient. That portion is used invasively on the patient during the medical procedure. The other portions of the instrument are non-invasive, that is, those portions of the instrument do not puncture, cut or penetrate into the tissue, bone or other body parts of a patient, typically these are the instrument handling surfaces and surfaces adjacent to the handling surfaces. Preferably the method of the present invention is used to color code the noninvasive portion of a medical instrument. Most preferably, the noninvasive portion which is color coded is the handling surface. However, areas near the handling surface may also be color coded. By handling surface is meant a portion of the medical instrument held by the user of the instrument to manipulate the instrument or to support the instrument or to hold the instrument. Typically this is the handle of the instrument. Other medical metal instruments may be part of a set to hold other sterile instruments, sterile drapes, sterile towels, sterile sheets or other sterile materials used during a surgical procedure, and as such do not have an "invasive" portion, but do have a handling surface or grasping part for hand manipulation of the instrument. These devices are within the scope of the present invention.

Thirdly, a water-borne polyurethane coating is electro-deposited onto the surface of the metal portion of the instrument in a micro thin layer. The coating maintains its integrity against chipping, peeling, breakage and striking after being exposed to normal rubbing. Typically, the coating is thick enough to adhere to the medical instrument but not thick enough to crack or to flake off of the medical instrument. Preferably the thickness of the coating deposited of the present method is from 0.1 mils to 0.5 mils, with the most preferred thickness being 0.2 mils to 0.3 mils. The thickness of the coating layer electro-deposited, depends upon the amount of time the instrument is subjected to electro-deposition and the charge applied to the instrument in the electro-deposition bath. This method of identifying sets of medical instruments may be used to identify both new and existing stainless steel, aluminum, chrome, and/or silver plated medical instruments. Because of the thinness and clarity of the electro-deposited polyurethane coating layer, for titanium medical instruments where "blue tinted" titanium is used, the underlying base of the "blue tinted" titanium metal will add a blue tinge to the color of the electro-deposited layer.

The preferred electro-deposition process is believed to involve the following steps. Preferably, the metal instruments are prepared for the electro-deposition of the coating as follows:

The instruments are first cleaned. Dirty used instruments are cleaned by washing in a hot soapy bath to remove debris, such as saline, protein residue or blood stains. New or refurbished instruments are cleaned by using a conventional bead blasting technique on the instruments. After cleaning, the instruments are pretreated in a bath of soapy water followed by a warm deionized water rinsing bath. Areas of the medical instrument are masked with TEFLON® tape to prevent electro-deposition of coating in those areas. The instrument is attached to an electrical lead. The instrument is placed in the colored aqueous polyurethane resin solution. The coloring in the colored water-borne polyurethane coating is believed to be due to the presence of polyurethane-compatible pigments, dyes or other coloring agent. The other electrical lead is placed in the solution. An electrical current is applied between the two leads and the colored polyurethane coating material is electro-deposited onto the unmasked metal surfaces of the instrument. To electro-deposit the coating, preferably three ampere of current is applied for 0.5 to 5 seconds or more, depending upon the weight of the instrument. After the material is electro-deposited on the unmasked surface of the instrument, the instrument is removed from the solution.

Finally, the instruments are cured in air at 270°–350° F. for a period of 2–50 minutes depending on weight of the instrument. Preferably the curing step occurs at about 320° F. for 3–20 minutes. The curing step is believed to be complete when the polyurethane compound cross links with the other pigment and dye compounds, but yet remains flexible.

Where a number of different colored coatings are desired on a metal medical instrument, it is important to mask areas of the instrument where no electro-deposition is to occur. Additional color coated regions may be added to this surface by preparing the instrument as previously described beginning with the step of rinsing the instrument in the deionized water rinsing bath, and then using a different colored aqueous polyurethane resin solution and following the remaining steps to electro-deposit a differently colored coating layer on the medical instrument. The second coating will not bond to the first coating as the first coating isolates itself from the electric charge. Therefore it is not necessary to mask an already color coated area on the medical instrument. Additional colored areas may be electro-deposited by repeating the process as previously described in different colored aqueous polyurethane resin solutions. In this manner, multiple different colors may be applied to a single instrument with each color being identified with a different surgical or medical purpose, or user or medical department or medical instrument set or any other parameter predetermined by the user. Depending upon the color plan created, an instrument may be identified as being useful for a number of medical procedures, users, manufactures and or departments. The user may have other categories for which colors are assigned. The instrument's color coding then can be visually recognized by a user and the instrument identified and sorted into different sets or tray set-ups. After the medical procedure, the instruments can easily be identified by the colors to specify cleaning, handling, maintenance, and/or repair procedures. This method is also well suited for inventory control purposes and lends itself well to situations where confirmation of the instrument is needed where loss or theft of instruments has occurred. In a practice of the invention, hospital departments can be provided with their own instrument colors so after the instruments are returned for repair or sterilization, the instruments can be quickly sorted and returned.

In addition, the coating can be readily and easily identified under normal incandescence and fluorescent hospital or clinic lighting systems; thus, no special excitation lighting systems are required to utilize this method of instrument identification. Also, since the coating is easily applied to large surfaces, i.e. handles, grasping surfaces, areas adjacent to either of these and other noninvasive portions of the medical or surgical instrument, it is not necessary for a user or maintainer of the instrument to spend a large amount of time identifying a small area of a color coded portion such as a taped colored chip or to recognize a specific geometric shape as indicating an instrument as belonging to an instrument set. The instrument can quickly be identified using the presently disclosed inventive method.

A particularly preferred water-borne polyurethane resin system for metal coating applied by electro-deposition useable in the present invention is commercially available from Rez-Tech, Inc. of Schofield, Wis., USA and Salisbury, N.C., USA and from Custom Glass Products, Schofield, Wis., USA. We believe that the water-borne polyurethane resin coating is commercially available from Rez-Tech, Inc. under the tradename VIRACOAT.

The electro-deposition of polyurethane provides an even, controlled thickness over metals commonly used for surgical equipment such as stainless steel, aluminum, chrome or silver plate, providing a colored indicia on the unmasked metal surface. The electro-deposited colored water-borne polyurethane coating indicia is peel resistant, capable of being multiply autoclaved and is conformable to a contour of the surface of the instrument. However, the polyurethane system is not as effective with instruments having a substantial percentage of "blue tinted" titanium, as was previously explained. The electro-deposited polyurethane coating adheres especially well to surgical grade, e.g. 410/420 grade, stainless steel (s.s) medical instruments. Typically very thin coatings are preferred. These are referred to as micro thin layer thickness. For micro thin layer thickness, the coating is thick enough to adhere but not so thick as to crack or to flake off the instrument. Preferably the coating on the stainless steel instruments ranges from 0.1 mils to 0.5 mils, most preferably 0.2 mils to 0.3 mils. The extreme thinness of the coating layer is especially advantageous on portions of the instrument that cooperate with one another. The coating is bendable; thus, it will not chip, peel or crack. The coating does not run or tear and is easily tinted to provide colors which contrast with the metals of the instruments. Presently, the coating is available in at least the following colors: violet, white, raspberry, green, brown, yellow, orange, purple, gold, bronze, blue, red violet, gun metal grey, red, black and copper. The colors are also available in shades and pearlescent shades of the aforementioned colors. The coating can be applied in the multitude of colors and it can be applied to old medical instruments since it does not require the new specially treated surfaces of stainless steel for application.

The colors of the coating may be selected from this group of colors according to a color plan to designate a medical specialty area, a specific physician user, a specific medical procedure, even a manufacturer of medical instruments or any other classification a user may desire. The color plan may be as simple or as complex as desired by the user.

For example, a medical specialty department may pick a main color, such as orthopedics picking the color green or neurosurgery picking the color purple. Then an additional set of distinguishing colors may be applied for each physician user. For example, black and white stripes may indicate the Chief of Staff of orthopedics. Yet another set of colors may indicate the medical procedure for which the instrument is used. For example, gold for an instrument used for hip replacement. Thus on one instrument there may be four colored indicia electro-deposited thereon, green, gold, black and white thus indicating that the instrument is an instrument belonging to the orthopedics department, used for hip replacement surgery and used in surgical procedure trays for patients operated upon by the chief of staff of orthopedics.

Where an instrument may be useful for a number of procedures for different medical departments, the colors of the coating may be selected to identify specific medical departments. For example, the instrument could be a set of surgical scissors which could be useful for an obstetrical gynecological (OBGYN) procedure or for an ear, nose and throat (ENT) procedure. In this case, one color such as yellow may be selected by the OBGYN clinic and another color such as blue may be selected by the ENT clinic. The individual set of surgical scissors could be color coated with blue and with yellow according to the present method to permit both colors on selected portions of the instrument.

Unlike standard metal electroplatings, the polyurethane coating is environmentally preferred because it is a water-based process of very low flammability and because there is virtually no effluent discharge. Because the electro-deposition of the coating does not create chemical waste water or hazardous emissions, the costs of applying the coating are lower.

The polyurethane coating is resistant to chemicals used in sterilization such as CIDEX® and to abrasion. The coating as applied to medical instruments is so durable that it has withstood 500 autoclave sterilization cycles without damage to the integrity of the coating, i.e., the coating has not chipped, broken, peeled or cracked after being applied to medical instruments which were subjected to steam autoclaving at 270° F. for 35 minutes at approximately 30 pounds per square inch of pressure. This time does not include the drying time.

The color coding materials are applied to metal surface portions of the instrument and preferably to noninvasive surface portions of the instrument such as the handle and/or adjacent surfaces. There are a wide variety of handle designs and permutations in design of hand held medical instruments. Some instrument handles require merely grasping the handle to work the instrument. These instruments typically have a single end for invasive work on the patient with the non invasive handling surface end oriented opposite the invasive end. Examples of single-ended instruments include, but are not limited to, ear curettes, single ended Wilder lachrymal dialators, trephines, general operating room knives, Canfield tonsil knifes; Sims uterine curettes and sounds, vaginal retractors, single ended mucous membrane knives, septum knives, cotton applicators, delicate retractors, delicate hooks, single ended retractors, Volkman retractors, Koerte retractors, Middeldorpf retractors, Billroth retractors and Meyerding retractors. Other instruments have two somewhat opposite oriented invasive ends with a handling surface disposed between the invasive ends. Examples of double ended instruments include, but are not limited to, double ended retractors, double ended mucous membrane knives, nasal periosteum elevators, Freer septum elevators, Roger septum elevators, double ended Freer septum knifes, double ended uterine curettes, Bowman lachrymal probes, and Hund dissector and pillar retractors. Yet other instrument have handles with finger ring portions and shank portions which are manipulated pivotally to one another to cause motion of blades or jaws. Examples of these instruments include, but are not limited to operating scissors, dissecting scissors, needle holders, Beckman thyroid retractors, perineal retractors, stitch scissors, sponge holding forceps, hemostatic forceps, tissue forceps, sterilizer forceps for instruments, and nasal septum cutting forceps, homeostatic forceps, tissue/sponge forceps, Hartman polypus forceps and Ballenger tonsil seizing forceps. Some of these instruments have ridged intermating portions, rachets, to lock the positioning of the invasive part of the instrument. Still, other instruments have a tweezers like configuration with a flattened spring handle which is held closed by exerting pressure between the users's thumb and fingers. These instruments include, but are not limited to, tissue forceps, dressing forceps, artery clamps, Bishop Harmon forceps, Castroviejo tying forceps, McPherson forceps (with tying platform), Capsulotomy forceps, Grafe fixation forceps (with spring catch), Guyton-Noyes fixation forceps (with slide catch), Guyton-Noyes fixation forceps (curved sideways with slide) Prince Strabismus (muscular advancement forceps), Ayer Chalazlon forceps (with set-screw), bulldog clamps, and towel clips. Yet, still other instruments have other types of handle geometry requiring springs, latching catches, or locking devices. Other instruments are permutations of the above instrument types, for example, but limited to Barraquer Iris scissors, Beckman thyroid retractors, Gelpi perineal retractors, and Barraquer suture forceps. The surfaces of the handles and adjacent areas may be smooth surfaces or they may be complex in nature, having textures, convolution, ridges, knurling or may have convex and or concave regions. The sizes of the instruments may vary, depending upon the application. Instruments being used for micro surgical techniques necessarily small, whereas other instruments, for example for abdominal surgery, being large. The present invention comprehends the full range and variety of hand held medical instruments used in medical and surgical procedures.

Because the coating is so thin and strong it can be applied to instruments having cooperating portions, sliding, interlatching, springing or locking portions as well as spring handled instruments. It comprehends such instruments but is not limited to, nasal septum cutting forceps, vena arteria bulldog clamps, Troutman-Chris scalpels, bladebreaker scalpels, Litchtenberg suture needleholders, Zweifel suture needleholder, Eiselberg-Mathieu suture needleholders, Henley selfretaining retractors, Seutin bandage cutting scissors, Mastoid Rongeurs, Castroviejo needleholder with lock, Barraquer needle holder with lock, Vannas after-cataract scissors, Holth corneoscleral punches, Vienna Nasal Specula, and Kalt Needle Holders; as well as to instruments used in micro surgery, such as, but not limited to micro forceps, aural micro surgical instruments, Trautman and Reill microneedleholders with pen-type handles, Castroviejo microneedleholders, Paton micro-needle holders, Arruga microneedle holder, Kalt micro-needle holder, Kalt-Arrugua microneedle holder, Castroviejo-Kalt micro-needle holder, Stevens microneedle holder, Polts-Smith micro-needle holder, and alligator forceps. The invention comprises all other types of medical instruments not fitting neatly into the above categories or permutations thereof, these include, but are not limited to, pelvimeters, Grones vaginal specula (where the pieces of the assembly may be color coded and reassembled), Berlind-Auvard vaginal specula, the individual specula of a Bruenings magnifier otoscope set, nasal polypus snare, the universal handle for interchangeable forceps, the noninvasive end of a removable needle and the handle of the Young-HRYNTSCHAK needle holder, selfretaining retractors of the Finsen, Alm, Jansen, Snitman, Allport and Henley types, abdominal retractors of the Balfour, Denis Browne, the O'Sullivan-O'Connor, Doyen and Fraz types. The coating may be applied to all areas of the handling surface or only to portions thereof, depending upon the color plan created. The coating may be applied to smooth surfaces as well as to those with complex surface characteristics. It is also useful for adherence to knurled surfaces which have fine ridges or beads which conventional tapes or coatings obscure. Knurling is frequently used on handles of micro surgical instruments or single ended instruments, such as Joseph delicate hooks. These are only examples and are not intended to limit the scope of the invention. Knurling or fine texturing of the handles of delicate small instruments is done to ensure extra gripping ability by the user. Conventional TEFLON®, nylons and plastic coatings and tapes have problems with being too thick, and obscuring the knurling surface texture. Paint has the disadvantage of chipability. Because of the advantageous micro thin thickness of the electro-deposition polyurethane coating, the knurling surface texture on the instrument is not obscured by the coating, but is maintained. In addition, the device may be used on instrument handles having complex surface characteristics such as convolutions. These instrument handles include, but not limited to, handles of specula, retractors, elevators, osteotomes and enucleation spoons of orthopedics instruments, obstetrical forceps, Richardson (Kelly) retractors. The coating may also be applied in bands around shanks of instruments such as those on forceps or scissors as well as the handles and shanks of forceps or scissors. The thinness of the layer permits the abutment of the shank portions of where shank portions abut when the instrument is closed, as for example in scissors or in forceps. Thus, different colored bands or stripes are electro-deposited on the instrument, with each band denoting a specific medical procedure, medical department, particular physician user, or instrument set manufacturer or a combination thereof.

Thus, the present invention comprehends a medical instrument having colored indicia on a metal surface thereof, the indicia comprising electro-deposited colored-water borne polyurethane coating, the indicia being peel resistant, capable of being autoclaved and conformable to a contour of the surface. Preferably, the metal surface is stainless steel, aluminum, chrome or silver plated and the indicia is electro-deposited thereon. The indicia is electro-deposited onto a handle portion of the instrument. The invention further comprehends that a second indicia comprising a differently colored water-borne polyurethane coating is electro-deposited adjacent to the first indicia on the metal surface of the instrument. Although, if desired, the indicia may be spaced from one another, according to the plan of the user. The invention still further comprehends that a plurality of indicia comprising differently colored water-borne polyurethane coatings are electro-deposited on a metal surface of the instrument.

The medical instrument may be double ended with the metal grasping surface disposed centrally between the ends and with the indicia electro-deposited on a portion of the metal surface. Alternatively, the medical instrument is a spring handled type instrument or the medical instrument is a micro forceps or the medical instrument has a knurled metal surface.

Preferably, the indicia is electro-deposited onto a stainless steel medical instrument.

Since multiple colors can be used on a surgical instrument, the instrument, therefore, is color coded for different procedures and for incorporation into different medical procedure kits or trays which can be delivered to various surgical suites or various clinic examination rooms. The invention further comprehends a kit of medical instruments comprising a collection of medical instruments selected for a specified medical procedure, each of the medical instruments having one commonly colored indicia on a metal surface thereof, the indicia comprising electro-deposited colored water-borne polyurethane coating, the indicia being peel resistant, capable of being autoclaved and conformable to a contour of the surface, the color being used to identify the specific medical procedure, each coating deposited in a micro thin layer thickness, the color of the coating contrasting with the instrument and where more than one colored coating has been electro-deposited, each colored coating also contrasting with any other colored coating.

The kit of the present invention also includes instruments having at least one additional differently colored indicia, with the additional differently colored indicia indicating the instrument may be also be used in another kit for a different medical procedure or the indicia may indicate that the instrument belongs to a particular medical specialty group or the indicia may indicate that the instrument is used by a particular medical user or the indicia may indicate that the instrument is produced by a particular manufacture or may be a combination of these.

The present invention is further explained by the following descriptions of the coating available from Rez-Tech, Inc. (Schofield, Wis., U.S.A.) as applied to different medical instruments, these descriptions should not be construed by way of limiting the scope of the present invention.

Figures 1A, 1B, 1C:
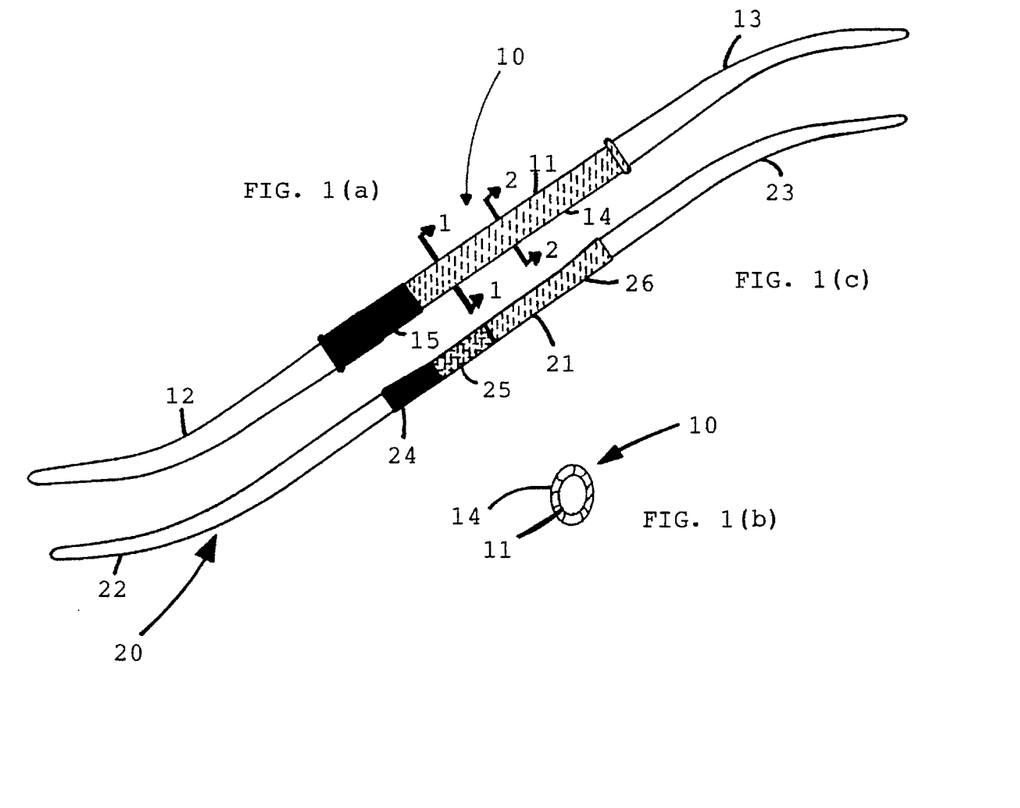
FIG. 1(a) is a side view of a double ended medical instrument having the colored coded coating applied to the handling surface.
FIG. 1(b) is a cross sectional view of the double ended medical instrument of FIG. 1(a) taken through the handling surface at section line 1—1 showing the colored coded coating as applied to the handling surface in that portion of the instrument located between section lines 1—1 and 2—2.
FIG. 1(c) is a side view of a double ended medical instrument having the colored coded coating applied to the handling surface, having three distinct colors being used.

FIGS. 1(a)—1(c) illustrate instruments of the double ended type.

FIG. 1(a) illustrates a double ended medical instrument 10, a uterine dilator, having a center portion 11 between two ends 12, 13. The ends 12, 13 are used invasively on the patient and the center portion 11 is noninvasive. The center portion 11 is a handling surface for the user to grasp while manipulating the instrument in the patient. A water-borne polyurethane coating was electro-deposited on the surface of the center portion 11 of the instrument 10 in a micro thin layer 14 according to the method previously described. A second different colored coating 15 was electro-deposited adjacent the first coating 14. For example, the first coating 14 is purple in color and the second coating 15 is black. Preferably the thickness of the layer 14 is 0.1 mils to 0.5 mils and most preferably 0.2 mils to 0.3 mils thick.

FIG. 1(b) is a cross sectional view of a double ended medical instrument 10 of FIG. 1(a) taken through the center portion 11 at section line 1—1 showing the colored coded coating layer 14 electro-deposited on the center portion 11. The view is a limited cross-sectional view of the instrument between section lines 1—1 and 2—2. The thickness of layer 14 is greatly exaggerated for illustration purposes. This type of identification management method may be used on both new and old instruments. The first color may cover all or a portion of the noninvasive surface of a medical instrument, a second color may be electro-deposited adjacent the first color where the first color covers only a portion of the noninvasive surface. This method of applying color coded coatings may also be used on other double ended instruments as are known in the hand held medical instrument art.

FIG. 1(c) is a top side elevational view of a second double ended medical instrument 20 having three differently colored color coded coatings 24,25,26 applied to the noninvasive portion 21. Invasive ends 22,23 are not coated. For example, the coating colors may be black 24, gold 25 and purple 26.

Figure 2A:
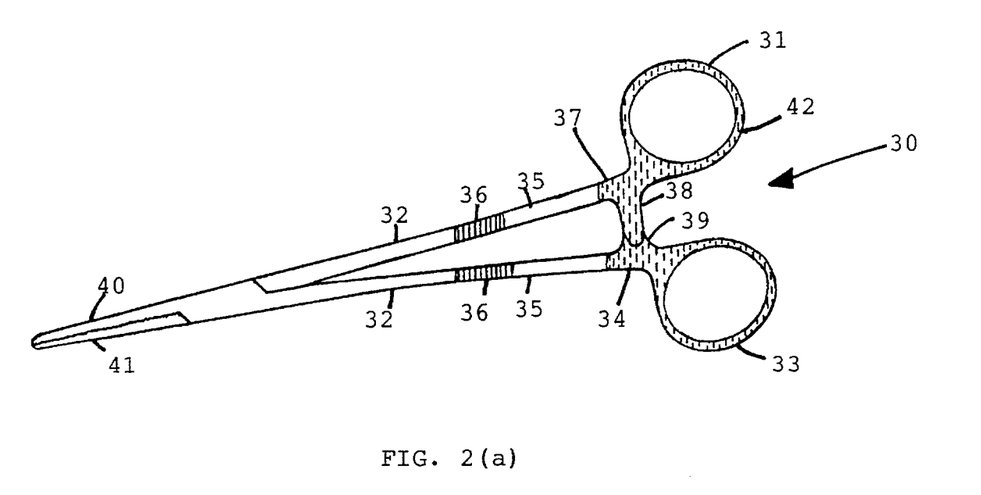
FIG. 2(a) is a top view of a medical instrument having the colored coded coating applied to the handling surface, with three distinct colors being used.

FIGS. 2(a)–2(g) illustrate instruments of the type having finger rings and shanks with pivotal blades or jaws. FIG. 2(a) illustrates an alternative embodiment whereby the color coded coating materials 34,35 and 36, have been electro-deposited onto the finger rings 31,33 of handle 42 and narrow shank portions 32 of a medical/surgical forceps instrument 30. Preferably the handle finger ring portions 31,33 and a small portion of the adjacent shaft 37 and the interlocking rachet portions 38, 39 were coated with one color coded coating 34. The long narrow shank portions 32 were coated with differently colored coded coatings 35,36. For example, the coating colors may be purple 34, white 35 and red 36.

Figure 2B:
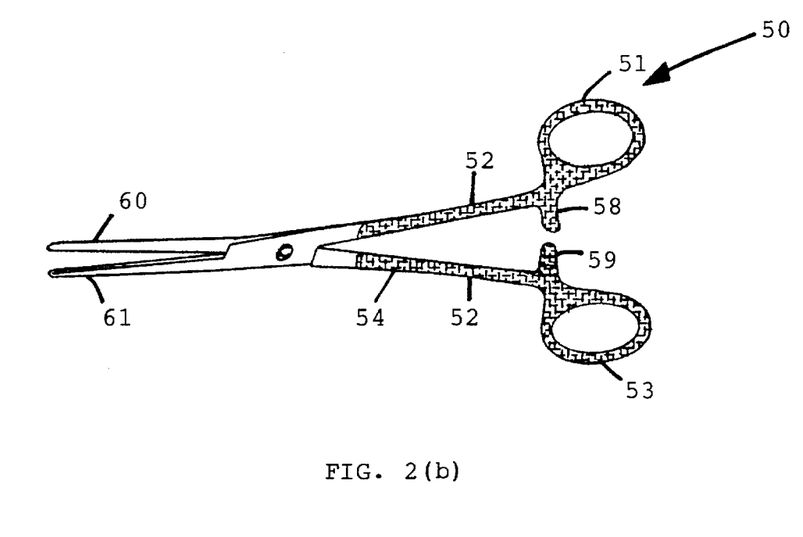
FIG. 2(b) is a top view of a medical instrument having a single colored coded coating applied to a handling surface.

FIG. 2(b) illustrates an alternative embodiment of the present invention showing a surgical forceps 50 in the open position with a single colored coded coating material 54, for example yellow in color, applied to the finger rings 51,53, rachets 58,59 and shanks 52,52. The jaws 60,61 are not color coated. Alternatively the location of the color coded coating material may be selected to cover only one of the finger rings 51,52, (not shown) or both finger rings 51,52, (not shown) or only one or both of the shanks 52, (not shown) or one of the shanks 32, and one of the finger rings 51,53 (not shown). Alternatively two color code coatings may be deposited on a finger ring (not shown). The selection and locations of the color coded coatings depend upon the needs and plan of the user of the instrument.

Figure 2C:
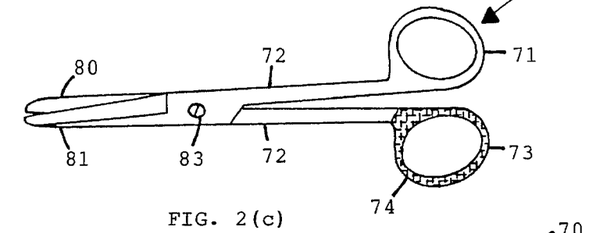
FIG. 2(c) is a top view of a medical instrument having a single colored coded coating applied to a handling surface.
Figure 2D:
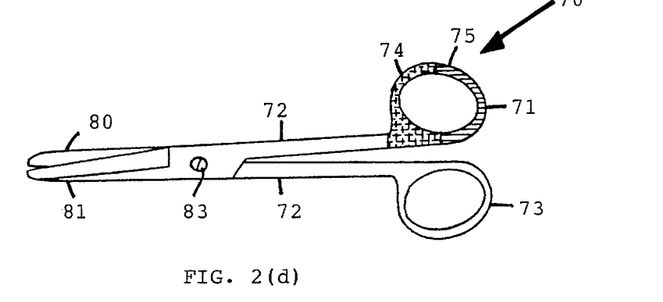
FIG. 2(d) is a top view of a medical instrument having the two colored coded coatings applied to a handling surface.

The placement of the color coded coating may be varied according to the plan of the user as shown in FIGS. 2(c) to 2(g). For example, FIG. 2(c) is a top view of a surgical scissors medical instrument 70 having a single colored coded coating 74, for example yellow in color, applied only one of the finger rings 73 of the handle portion. Alternatively two different color coded coatings 74,75 may be used on one finger ring 71 as shown in FIG. 2(d). For example, coating colors may be yellow 74 and blue 75.

Figure 2E:
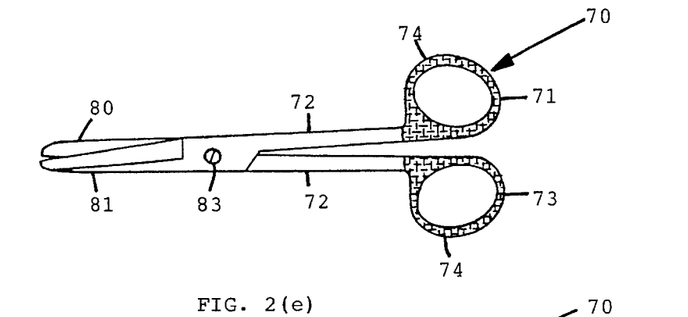
FIG. 2(e) is a top view of a medical instrument having a single color coded coating applied to the handling surface.

Another example of the choice of application of the coating material according to the present invention is illustrated in FIG. 2(e) where a scissors 70 has the colored coded coating 74, for example yellow, applied to both finger rings 71 and 73.

Figure 2F:
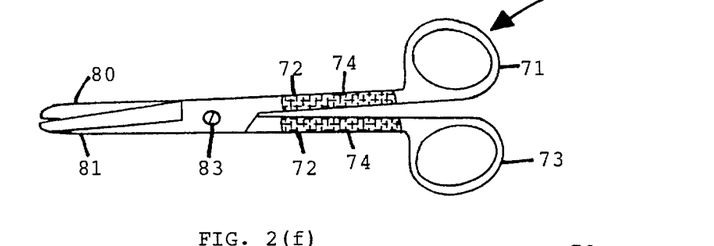
FIG. 2(f) is a top view of a medical instrument having the colored coded coating applied to the noninvasive shank surfaces.
Figure 2G:
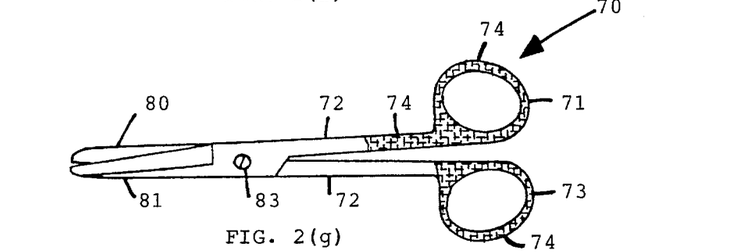
FIG. 2(g) is a top view of a medical instrument having the colored coded coating applied to the handling surfaces and to one of the noninvasive shank surfaces.

Yet another illustration of the varied plan of the user is to apply the colored coded material as illustrated in FIG. 2(f) where the colored coded coating 74, for example yellow in color, is applied to the noninvasive shank surfaces 72,72. Still another instance of selection of the location is shown in FIG. 2(g) where the colored coded coating 74, for example yellow in color, is applied to the finger ring 71,73 and to one of the noninvasive shank surfaces 32. As was previously discussed, instead of a single colored coating area, multiple color coded coatings may be employed according to the plan of the user.

Figure 3A:
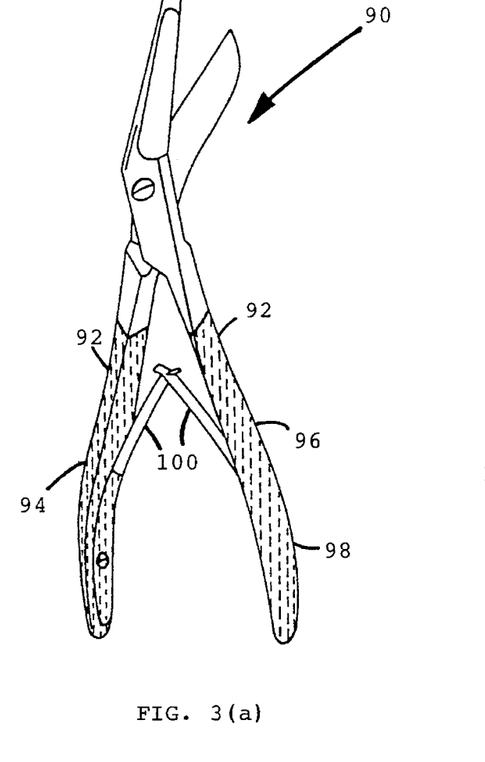
FIG. 3(a) is a perspective view of a medical instrument of a spring handled type with the color coded coating applied to portions of the handling surface.
Figure 3B:
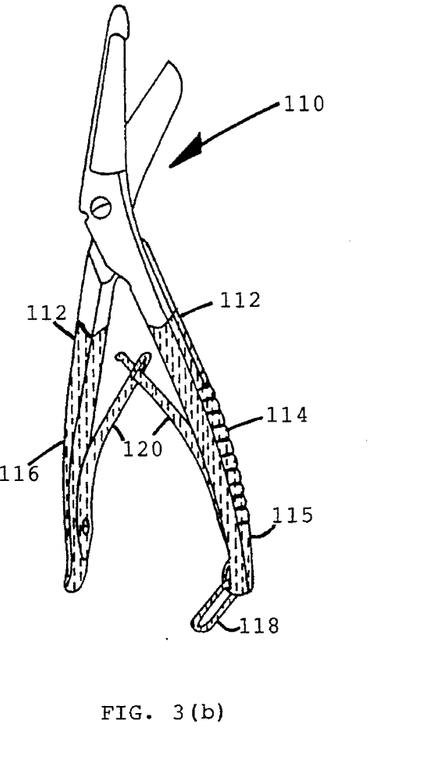
FIG. 3(b) is a perspective view of a medical instrument of a spring handled type with the color coded coating applied to portions of the handling surface and spring.
Figure 3C:
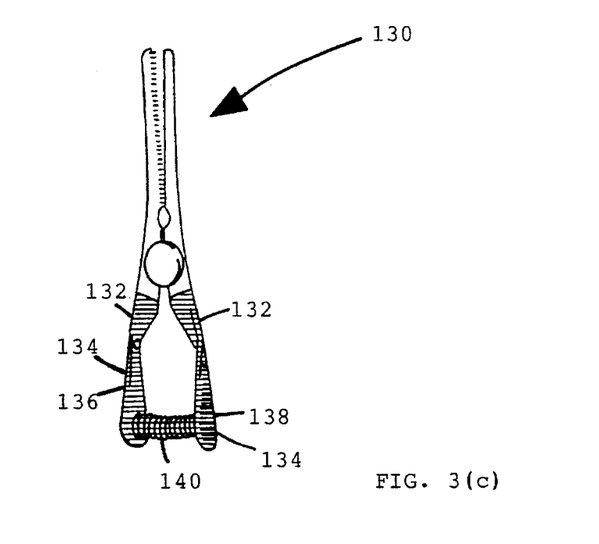
FIG. 3(c) is a perspective view of a medical instrument of a spring handled type with the color coded coating applied to portions of the handling surface and spring.

FIGS. 3(a)–3(c) illustrate spring handled instruments of the present invention. This method of applying the color coded coating may be used on instruments such as, but not limited to Graefe fixation forceps with spring catches, mastoid rongeurs, Vienna nasal specula, and Kalt needle holders.

FIG. 3(a) illustrates an alternative embodiment of the present invention showing a spring handled type medical instrument. The spring handled bandage scissors 90 shown in FIG. 3(a) with the color coded coating 92, for example purple in color, applied to handle 98 portions 94,96. With spring handled type medical instruments the coating is not easily damaged by the spring 100 action. The coating on the instrument remains free of breaks, cracks or tears.

FIG. 3(b) shows a top view of a medical instrument of a spring handled type 110 with the color coded coating 112, for example purple in color, applied to handle 115 portions 114,116, spring 120 and locking loop 118; and FIG. 3(c) shows a top view of a medical instrument 130 of a spring handled type with the color coded coating 134, for example blue in color, applied to portions of the handling surface 136,138 and spring 140.

Figure 4:
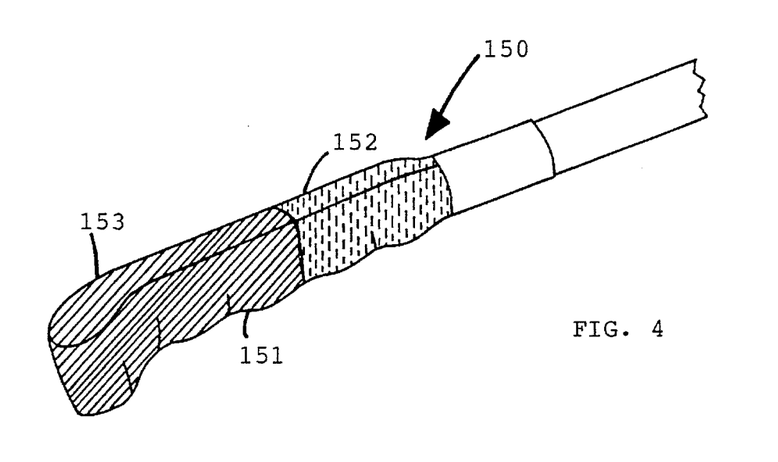
FIG. 4 is a partial perspective view of a medical instrument having complex surface characteristics having the color coded coating applied to the handling surface.

FIG. 4 illustrates yet another alternate embodiment of this invention and shows the partial perspective view of a single ended medical instrument 150 with the color coded coatings 152 and 153 (for example in colors purple and brown respectively) electro-deposited on the handling surface 151. This instrument is a single ended instrument with the invasive end not shown. Because of the complex surface characteristics of the handle, it is very difficult to apply conventional coating materials or to adequately attach tape to the ridges of the surface. The inventive coating was electro-deposited thereby forming a uniform micro thin layer.

Figure 5A:
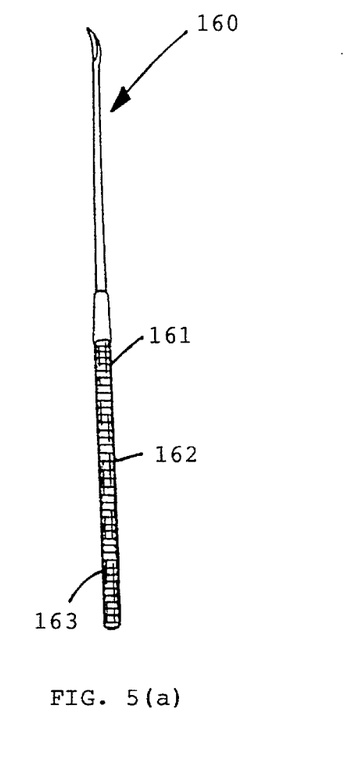
FIG. 5(a) is a perspective view of a medical instrument of the micro medical instrument type with the color coded coating applied to the handling surface.

FIG. 5(a) illustrates still another alternate embodiment of the present invention and shows the side view of a micro medical instrument 160, an aural elevator, used in micro surgery. The inventive coating 162, for example blue in color, is applied to the handling surface 161 of this single ended micro instrument. Advantageously the knurling 163 on the handling surface 161 of this micro medical instrument 160 is not obscured by the micro thin color code coating layer 162 of the present invention.

Figure 5B:
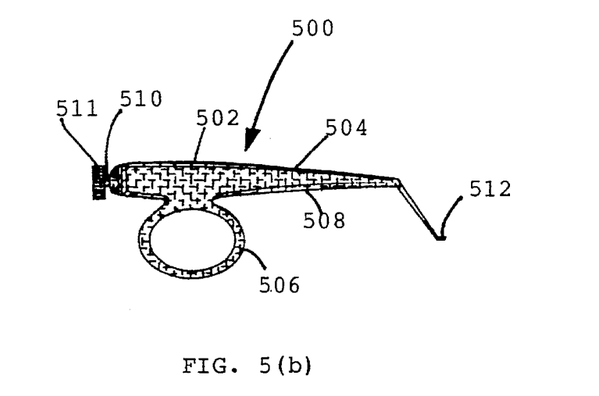
FIG. 5(b) is a side view of another micro medical instrument in the closed position with the color coded coating applied to the handling surface.
Figure 5C:
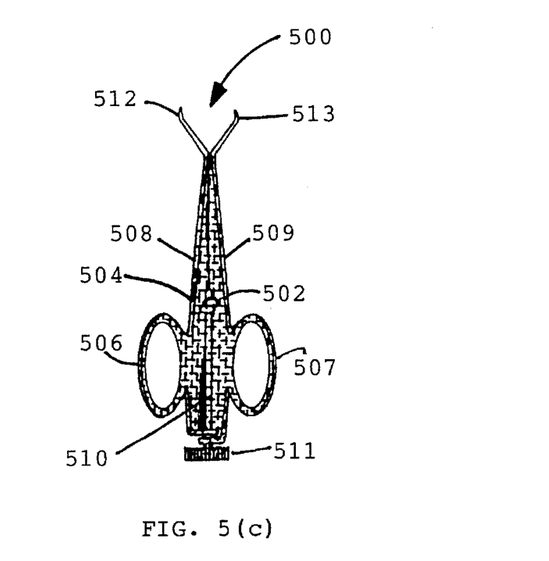
FIG. 5(c) is a bottom view of the micro medical instrument of FIG. 5(b) in the open position with the color coded coating applied to the handling surface and to the pin and pin head.

FIG. 5(b) illustrates a further alternative embodiment of the present invention and shows the side view of another micro medical instrument, a Butterfly Fixation forceps 500, used in micro surgery. The inventive coating 502, for example yellow in color, is applied to the handling surface 504 of this instrument 500. The instrument 500 has looped handles 506, 507 shafts 508,509 pin 510, pin head 511 and butterfly ends 512, 513. The looped handles 506, 507 are pressed together (closed position) and released (open position) to operate the butterfly ends 512, 513. The coating 502 is applied to the looped handles 506, 507 and shafts 508 and 509. The butterfly ends 512, 513 are not coated. The instrument is in the closed position with the looped handles 506, 507 and shanks 508, 509 abutting. FIG. 5(c) is the bottom view of the medical instrument 500 of FIG. 5(b) showing the looped handles 506, 507 and the entire shafts 508, 509 including the pin 510 and pin head 511 color coated with coating 502 according to the present invention. The instrument 500 is in the open position in FIG. 5(c). Micro instruments such as micro forceps are difficult to coat because of the small size and the cooperation of the parts. This method of applying color coding may be applied to micro surgical instruments such as, but not limited to, Castroviejo tying forceps, needleholders, and suturing forceps, McPherson forceps, Barraquer needleholders, and Vannas after-cataract scissors.

Figure 6A:
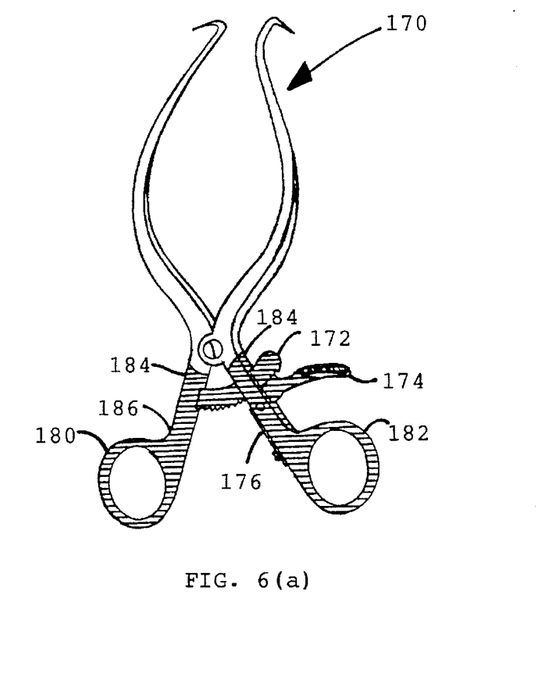
FIG. 6(a) is a perspective view of a medical instrument having a color coded handle and spring lock section.
Figure 6B:
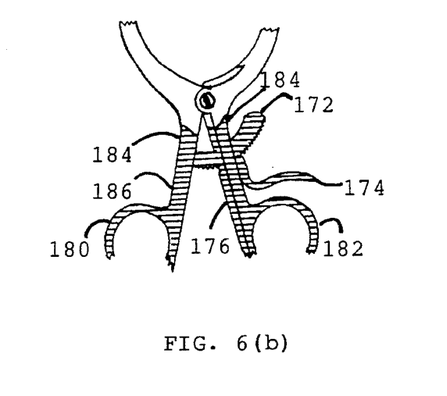
FIG. 6(b) is a partially enlarged and rotated view of the medical instrument of FIG. 6(a)

FIG. 6(a) illustrates still yet another alternate embodiment of the present invention and shows the side view of a medical instrument, an obstetrical perineal retractor, having interlocking features. As best shown in FIG. 6(b), the medical instrument 170 has a rachet 172 and spring lock 174. The spring clip 176, rachet 172, spring lock 174, the finger rings 180,182 and shanks 184,184 may be color coated according to the present invention with a color coating 186, for example, blue in color. The micro thin coating advantageously allows cooperation of the interlocking features.

Figure 7:
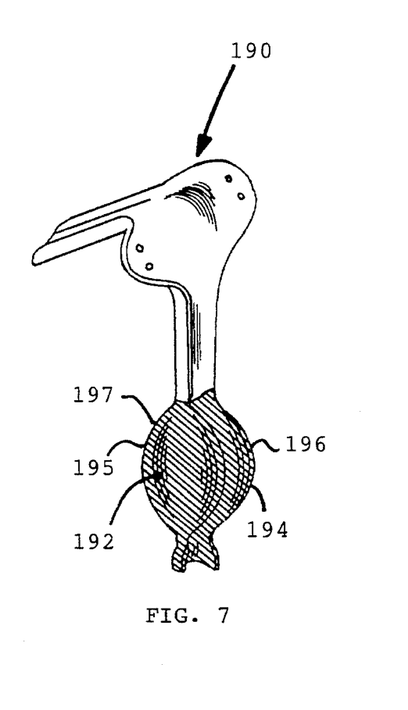
FIG. 7 is a perspective view of a medical instrument having complex surface characteristics.

FIG. 7 illustrates yet another embodiment of the present invention where the innovative coating 195, for example green in color, is applied to a medical instrument 190 having a complex surface 197. The coating 195 is applied to the peep grove 192 and large weighted volume 194 of the handling surface 196 of a Berlind—Auvard Vaginal speculum 190.

Figure 8:
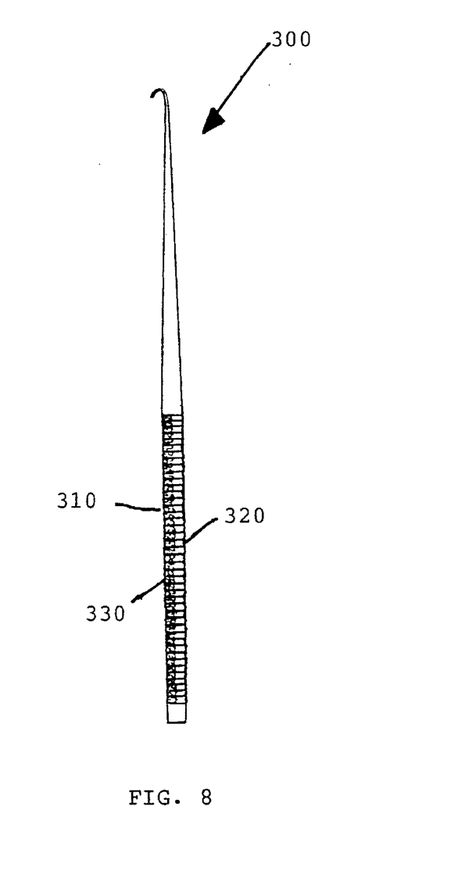
FIG. 8 is a side view of a medical instrument of the knurled handled type having the color coded coating applied to the handling surface.

FIG. 8 illustrates yet a further alternate embodiment of this invention and shows a side view of a knurled handled medical instrument 300, a Joseph fine hook retractor, with the color coded coating 310, for example blue in color, electro-deposited on the handle 320. Conventional paints and tapes obscure the fine detailing of the knurled surface, thereby losing the gripping surface caused by the knurling 330. The present invention deposits a micro thin layer advantageously maintaining the knurled gripping surface.

FIG. 9 illustrates an exemplary set or kit 400 of medical surgical instruments having the color coding identification system of the present invention. The exemplary set is a set of instruments prepared as a medical procedure tray for a radial keratotomy. However, the invention is not limited to this particular set of instruments but rather comprehends instruments collected according to sets selected by a user or a manufacture which instrument sets or kits are identified and marked as previously disclosed. The color coding on the noninvasive portions of the instruments are cross hatched to identify specific color combinations. For example, the handle surfaces of each of the instruments are color coded with a single color coating 420, for example blue in color, to denote that the instruments belong in a particular procedure tray. Alternatively the color coding could indicate that the instruments are produced by a particular manufacturer for a particular medical procedure. The instruments included in tray 400, are: solid Wire Speculum 401; double edge Diamond Micrometer 403; Thornton Fixation Ring 404; straight Fixation Forceps 405; angled Fixation Forceps 406; Visual Axis Marker 407; Optic Zone Marker 408; Radial Marker (6 Lines) 409; Radial Marker (8 Lines) 410; Incision Spreading Forceps 411; Incision Depth Gauge 412; Irrigating Cannula, (27 gauge) 413. The color coding material 420 is applied to the wire handling portion 415 of solid wire speculum 401. Other instrument sets could include, but are not limited to, an intra-capsular cataract extraction kit, an eye lid surgery kit, a muscle surgery kit, a vitro-retinal surgery kit, a glaucoma surgery kit, a planned extra-capsular cataract extraction kit, and a lacrimal surgery kit.

FIG. 10 provides an example of a medical instruments kit utilizing the multiple colored indicia of the present invention. The exemplary suture removal kit 900 has a knife 902, a pair of scissors 904, and two forceps 906,908. Each of the instruments 902,904,906,908 has an indicia 910, for example, in the color green, indicating that the instruments are suitable for grouping for a particular medical procedure, i.e., for use in a four item suture removal kit 900. Two of the instruments the knife 902, and forceps 906 have a second indicia 912, for example, in the color red, indicating that they are suitable for use in another kit for a different medical procedure. Two of the instruments, the knife 902 and the scissors 904, have an additional indicia 914, for example in the color blue, indicating that the instruments belong to a particular medical specialty. Two of the instruments, the two pairs of forceps 906,908, each have additional indicia 916, 917, for example in the color black and in the color white, indicating that the instruments are preferred by a particular user. One of the instruments 906 has a differently colored indicia 918, for example in the color violet, indicating that instrument is produced by a particular manufacturer. Thus kits can be produced that are tailored according to medical procedure, medical specialty group, instrument user, instrument manufacture or any other designation selected by the user.

The colors of the coatings selected in the above figures are illustrative and for purposes of example only and can be varied according to the plan of the user. The number of the different colored coatings applied and the location can also be varied according to the plan of the user.

While the present invention has now been described and exemplified with some specificity, those skilled in the art will appreciate the various modifications, including variations, additions, and omissions, that may be made in what has been described. Accordingly, it is intended that these modifications may also be encompassed by the present invention and that the scope of the present invention be limited solely by the broadest interpretation that lawfully can be accorded in the appended claims.

We claim:

1. A method of identifying sets of metal medical instruments comprising the steps of:
   a. selecting a color plan for identifying metal medical instruments for use for a specified medical procedure;
   b. providing at least one medical instrument having a metal portion;
   c. electro-depositing at least one colored water-borne polyurethane coating on said metal portion in accordance with said plan, each said coating being resistant to sterilization conditions, each said color of said coating contrasting with said instrument and, where more than one colored coating has been electro-deposited with any other said colored coating; and d. allowing each said coating to cure at a temperature in the range of 270° F. to 350° F. for a time period in the range of 2 minutes to 50 minutes.

2. The method of claim 1 wherein step b includes providing said instrument for electro-depositing said coating where said instrument is selected from the group consisting of stainless steel, aluminum, chrome or silver plated instruments.

3. The method of claim 1, wherein step c includes electro-depositing a plurality of differently colored water-borne polyurethane coating onto said metal portion of said instrument.

4. The method of claim 1 wherein said metal portion is a handling surface and wherein step c includes electro-depositing said coating onto said handling surface.

5. The method of claim 1 wherein said metal portion comprises a handling surface and another surface adjacent to said handling surface wherein step c includes electro-depositing said coating onto said surface adjacent to said handling surface.

6. The method of claim 1, wherein said metal portion further comprises a shank portion and wherein step c includes electro-depositing a plurality of colored water-borne polyurethane coatings on said shank portion of said instrument.

7. The method of claim 1, wherein said instrument is double ended with said metal portion disposed between said ends and wherein step c includes electro-depositing said coating material on said metal portion.

8. The method of claim 1, wherein step b includes providing a spring handled type instrument for electro-depositing said coating thereupon.

9. The method of claim 1, wherein step b includes provided a micro surgical instrument for electro-depositing said coating thereupon.

10. The method of claim 1, wherein step b includes providing a knurled handling surface for electro-depositing said coating thereupon.

11. The method of claim 1, wherein step c includes electro-depositing said coating onto a stainless steel instrument.

12. The method of claim 11 wherein said metal portion is a handling surface and wherein step c includes electro-depositing said coating on said handling surface.

13. The method of claim 12, wherein said handling surface further comprises a handle portion and wherein step c includes electro-depositing said coating on said handle portion of said instrument.

14. The method of claim 13, wherein step c includes electro-depositing another differently colored water-borne polyurethane coating adjacent to said coating on said handle portion of said instrument.

15. The method of claim 14, wherein said metal portion further comprises a shank portion and wherein step c includes electro-depositing a plurality of colored water-borne polyurethane coatings on said shank portion of said instrument.

16. The method of claim 11, wherein said instrument is double ended with said metal portion disposed between said ends and wherein step c includes electro-depositing said coating material on a part of said metal portion.

17. The method of claim 11, wherein step b said stainless steel instrument is a spring handled type instrument for electro-depositing said coating thereupon.

18. The method of claim 11, wherein step b said stainless steel instrument is a micro surgery instrument for electro-depositing said coating thereupon.

19. The method of claim 11, wherein step b said stainless steel instrument has a knurled handling portion for electro-depositing said coating thereupon.

20. The method of claim 1, further comprising the step of sorting said instrument into a set to be utilized for a specific medical procedure by grouping said instruments with other instruments similarly coated, wherein said instruments are selected for said sorting by said instruments possessing a common colored coating.

21. The method of claim 20, wherein said metal portion is a handling surface and wherein step c includes electro-depositing at least one said colored coating to substantially cover said handling surface, thereby allowing a user to easily identify the instrument without close scrutiny.

22. The method of claim 1, wherein step a includes selecting said colored coating of a color that is readily visible under normal hospital and clinic lighting conditions, and does not require special lighting to view the colored coating.

23. The method of claim 1, wherein said instrument has a non-invasive portion and an invasive portion and wherein step c includes electro-depositing said coating upon said non-invasive portion.

24. A medical instrument having colored indicia on a metal surface thereof, said indicia comprising electro-deposited colored water-borne polyurethane coating, said indicia being peel resistant, capable of being multiply autoclaved and is conformable to a contour of said surface.

25. The medical instrument of claim 24, wherein said coating maintains its integrity against chipping, breakage, peeling and sticking after 500 autoclave cycles, where said coating is maintained at 270° F. at approximately 30 pounds per square inch pressure in steam for approximately 35 minutes time.

26. The medical instrument of claim 24, wherein said coating is flashable at an autoclave sterilization cycle of said instrument using steam treatment under pressure of approximately 30 pounds per square inch at a temperature of 270° F. for a time period of 3 to 10 minutes depending a weight of said instrument.

27. The medical instrument of claim 26, wherein said metal surface is selected from the group consisting of stainless steel, aluminum, chrome or silver plated metal surfaces and said indicia is electro-deposited thereon.

28. The medical instrument of claim 26, wherein said indicia is electro-deposited onto a handle portion of said instrument.

29. The medical instrument of claim 26, wherein a second indicia comprising a differently colored water-borne polyurethane coating is electro-deposited adjacent to first indicia on said metal surface of said instrument.

30. The medical instrument of claim 26, wherein a plurality of indicia comprising differently colored water-borne polyurethane coatings are electro-deposited on separate areas of a metal surface of said instrument.

31. The medical instrument of claim 26, wherein said instrument is double ended with said metal surface disposed between said ends and with said coating material electro-deposited on a portion of said metal surface of said instrument.

32. The medical instrument of claim 26, wherein said instrument is a spring type instrument.

33. The medical instrument of claim 26, wherein said instrument is a micro surgical instrument.

34. The medical instrument of claim 26, wherein said instrument has complex surface characteristics.

35. The medical instrument of claim 26, wherein said indicia is electro-deposited onto a stainless steel instrument.

36. A kit of medical instruments comprising a collection of medical instruments selected for a specified medical procedure, each of said medical instruments having a commonly colored indicia on a metal surface thereof, said indicia comprising electro-deposited colored water-borne polyurethane coating, said indicia being peel resistant, capable of being autoclaved and conformable to a contour of said surface, said color being used to identify said specific medical procedure, each said coating deposited in a micro thin layer thickness, each said color of said coating contrasting with said instrument and where more than one colored coating has been electro-deposited, each said colored coating also contrasting with any other said colored coating.

37. The kit of claim 36 wherein said instruments have at least one additional differently colored indicia, said additional differently colored indicia indicating the said instrument may be also be used in another kit for a different medical procedure.

38. The kit of claim 36 wherein said instruments have at least one additional differently colored indicia, said additional differently colored indicia indicating the said instrument belongs to a particular medical specialty group.

39. The kit of claim 36 wherein said instruments have at least one additional differently colored indicia, said additional differently colored indicia indicating that said instrument is used by a particular user.

40. The kit of claim 36 wherein said instruments have at least one additional differently colored indicia, said additional differently colored indicia indicating that said instrument is produced by a particular manufacturer.

41. The kit of claim 36, wherein said micro thin layer thickness of said electro-deposited colored water-borne polyurethane coating comprises a layer thick enough to adhere to each of said medical instruments but not so thick as to crack or flake off each of said medical instruments.

42. The kit of claim 36, wherein said coating thickness ranges from 0.1 to 0.5 mils thickness.

43. A method of identifying sets of metal medical instruments comprising the steps of:
  a. selecting a color plan for identifying metal medical instruments for use for a specified medical procedure;
  b. providing at least one medical instrument having a metal portion;
  c. electro-depositing at least one colored water-borne polyurethane coating in a micro thin layer thickness on said metal portion in accordance with said plan, each said coating being resistant to sterilization conditions, each said color of said coating contrasting with said instrument and, where more than one colored coating has been electro-deposited with any other said colored coating, said micro thin layer thickness ranging from 0.1 to 0.5 mils thickness; and
  d. allowing each said coating to cure at a temperature in the range of 270° F. to 350° F. for a time period in the range of 2 minutes to 50 minutes.

44. The method of claim 43 wherein step c includes electro-depositing said coating in said micro thin layer thickness with said micro thin layer thickness ranging from 0.2 to 0.3 mils thickness.

* * * * *